Figure 1:
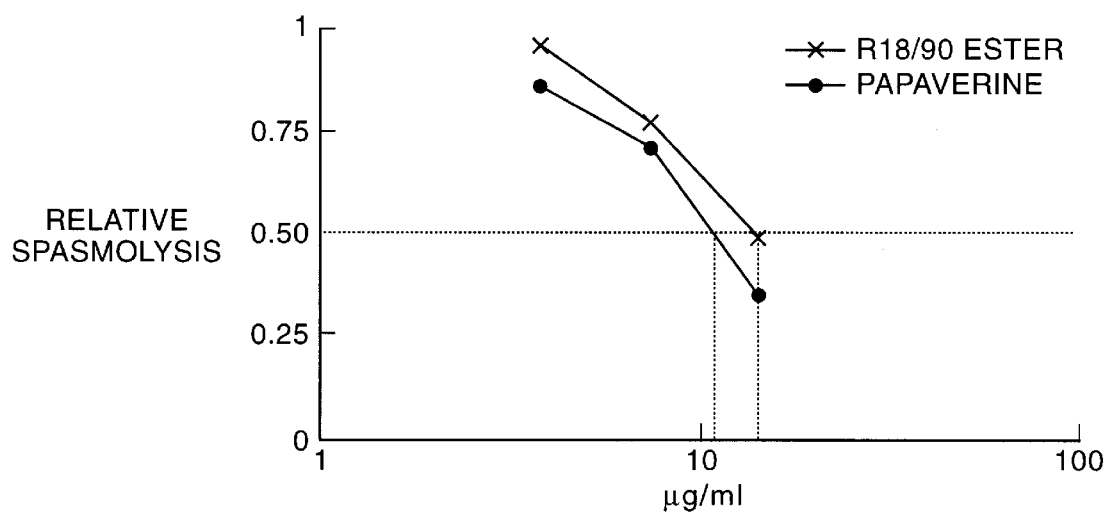

United States Patent

Pein et al.

[11] Patent Number: 5,897,875
[45] Date of Patent: Apr. 27, 1999

[54] USE OF α,α-DIPHENYLACETIC ACID-4-(N-METHYL-PIPERIDYL) ESTER AS A SPASMOLYTIC ANALGESIC

[76] Inventors: Eckhart Pein, Sohnreystasse 16, D-37154 Northeim; Helmut Ritter, Rotdornweg 37, D-42111 Wuppertal; Reinhard Laven, Lindenstrasse 10, D-38259 Salzgitter, all of Germany

[21] Appl. No.: 08/945,388

[22] PCT Filed: Dec. 14, 1996

[86] PCT No.: PCT/EP96/05627

§ 371 Date: Oct. 27, 1997

§ 102(e) Date: Oct. 27, 1997

[87] PCT Pub. No.: WO97/22343

PCT Pub. Date: Jun. 26, 1997

[30] Foreign Application Priority Data

Dec. 20, 1995 [DE] Germany ............... 195 47 621

[51] Int. Cl.[6] .................................... A61K 9/48

[52] U.S. Cl. .................. 424/451; 424/436; 424/464; 424/489; 424/494

[58] Field of Search .................. 424/451, 464, 424/489, 494; 514/183, 317

[56] References Cited

U.S. PATENT DOCUMENTS 4,678,780  7/1987  Davis ........................... 514/183
5,153,205  10/1992  Lotti ........................... 514/317

FOREIGN PATENT DOCUMENTS 0 445 731 A1  5/1991  European Pat. Off. .

*Primary Examiner*—Thurman K. Page
*Assistant Examiner*—William E. Benston, Jr.
*Attorney, Agent, or Firm*—Pillsbury Madison & Sutro LLP

[57] ABSTRACT

The use of α,α-diphenylacetic acid-4-(N-methyl-piperidyl) ester for the treatment of painful muscular cramp conditions in the region of the abdominal cavity or for the production of drugs for the treatment of painful muscular cramp conditions in the region of the abdominal cavity.

8 Claims, 1 Drawing Sheet

USE OF α,α-DIPHENYLACETIC ACID-4-(N-METHYL-PIPERIDYL) ESTER AS A SPASMOLYTIC ANALGESIC

This application is the national phase of international application PCT/EP96/05627, filed Dec. 14, 1996 which designated the U.S.

The underlying object of the present invention is to demonstrate a substance which is suitable for the treatment of painful spasms and dyskinesia of the smooth musculature in the region of the abdominal cavity, particularly in the peritoneal cavity, such as gall-stone colic, stomach and intestinal spasms, irritable colon and pylorospasm, and in the retroperitoneal cavity also, such as renal colic and urethral stone colic.

Prior knowledge of the pharmacological action of α,α-diphenylacetic acid-4-(N-methyl-piperidyl) ester, which is also hereinafter termed the "ester", was substantially related to its cholinolytic activity, which has been known since 1943 (J. Am. Chem. Soc., 65 (1943) 262–267). In addition, publications from 1988–1990 verify the high activity of α,α-diphenylacetic acid-4-(N-methyl-piperidyl) ester in relation to peripheral and central muscarine receptors of various organs (Eu. J. Pharmakol., 151 (1988) 83–96; Naunyn-Schmiedeberg's Arch. Pharmakol., 339 (1989) 145–151; Br. J. Pharmakol., 100 (1990) 395–397). German Patent Specification 42 05 843 C2 describes how α,α-diphenylacetic acid-4-(N-methyl-piperidyl) ester has a strong neurotropic-spasmolytic effect, i.e. cholinolytic effect, on the urinary bladder muscle, which anatomically and physiologically forms part of the pelvic contents, as well as exhibiting a slight central cholinolytic activity.

An investigation of the further pharmaco-dynamic properties of α,α-diphenylacetic acid-4-(N-methyl-piperidyl) ester has surprisingly and unexpectedly shown a pronounced musculotropic-spasmolytic effect on the organs of the abdominal cavity (abdomen), as well as the considerable analgesic effects of this compound.

The present invention therefore relates to the use of α,α-diphenylacetic acid-4-(N-methyl-piperidyl) ester or salts thereof with physiologically compatible organic or inorganic acids for the therapy of painful muscular cramp conditions, and to the production of drugs for the therapy of painful muscular cramp conditions, in the region of the abdominal cavity, particularly of muscular cramp conditions in the region of the peritoneal cavity, such as pylorospasm, gall-stone colic, stomach and intestinal spasms and irritable colon, and also of those in the retroperitoneal cavity, such as renal colic and urethral stone colic. This use is applicable to human and veterinary medicine.

Examples of physiologically compatible acids which can be employed for the use of salts include the organic and inorganic acids which are customarily used in pharmacology, such as hydrochloric acid, sulphuric acid, phosphoric acid or carboxylic acids and dicarboxylic acids. Examples of suitable organic acids include acetic acid, fatty acids such as stearic acid, lauric acid, oleic acid or palmitic acid, glycolic acid, lactic acid, pyruvic acid, malonic acid, succinic acid, fumaric acid, malic acid, tartaric acid, citric acid, cyclamic acid, ascorbic acid, benzoic acid, 4-hydroxybenzoic acid, cinnamic acid, salicylic acid and mandelic acid. Sulphonic acids are also suitable, such as methanesulphonic acid, ethanesulphonic acid and hydroxyethanesulphonic acid. The salts can be formed in the usual manner.

FIG. 1 illustrates the musculotropic-spasmolytic efficacy of the ester on *Taenia coli* isolated from the guinea pig, compared with that of papaverine. Barium chloride in a bath concentration of 0.2 mg/ml was employed as the spasmodic. The dose effect relation is illustrated as a function of the relative spasmolysis.

The $EC_{50}$ value for the ester was 12.6 μg/ml and attained the effective strength of papaverine.

The fact that the effect of α,α-diphenylacetic acid-4-(N-methyl-piperidyl) ester also comprises a powerful analgesic component was particularly unexpected and surprising. FIG. 3 illustrates the analgesic effect of the ester compared with that of the reference substance tramadol. The analgesic activity of the ester was determined by employing the usual hot plate technique. When administered subcutaneously to mice (body weight 20–25 g), the ester exhibited a dose-dependent analgesic effect, the level of efficacy of which corresponded to that of tramadol.

The surprising and unexpected pharmaco-dynamic effects of α,α-diphenylacetic acid-4-(N-methyl-piperidyl) ester show that this substance is a spasmolytic analgesic which makes possible the effective treatment of illness conditions in the region of the abdominal cavity which are characterised by muscular cramp conditions (gall-stone colic, stomach and intestinal spasms, irritable colon, pylorospasm, renal colic and urethral stone colic, and painful tenesmus due to radiotherapy in the abdominal and retroperitoneal region).

Figure 2:
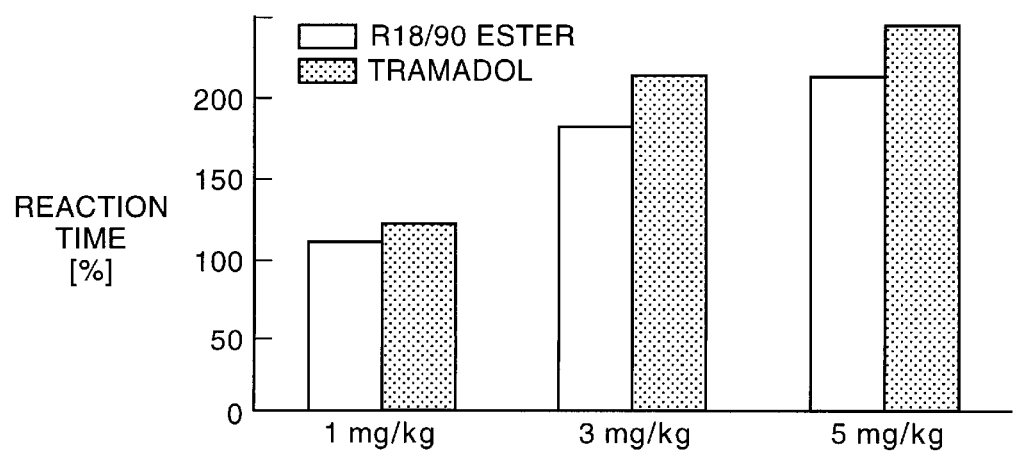

FIG. 2 illustrates the analgesic effect of the ester compared with that of tramadol in a hot plate test after subcutaneous application to mice.

The advantageous nature of the ester is due to the fact that the substance demonstrated here intrinsically combines the effective quality of an analgesic with that of a spasmolytic which has a musculotropic effect.

The ester which is used according to the invention can be administered in various ways, for example orally or parenterally. It can be administered in the form of powders, tablets, capsules, dragees or suppositories, or in an aqueous or oleaginous suspension. Some examples of formulations are given below.

The ester which is used according to the invention can be employed with other therapeutically effective substances, such as antibiotics and sedatives (tranquillisers).

EXAMPLES 1. 200 mg tablets

| | |
|---|---|
| α,α-diphenylacetic acid-4-(N-methyl-pipendyl) ester | 20mg |
| microcrystalline cellulose | 159mg |
| crosslinked poly-(N-vinylpyrrolidone) | 20mg |
| magnesium stearate | 1mg |

2. 300 mg capsules

| | |
|---|---|
| α,α-diphenylacetic acid-4-(N-methyl-piperidyl) ester | 20mg |
| yellow beeswax | 10mg |
| soya oil | 10mg |
| vegetable oil | 160mg |
| capsule shell | 100mg |

3. Injection ampoules

| | |
|---|---|
| α,α-diphenylacetic acid-4-(N-methyl-pipendyl) ester | 20mg |
| physiological NaCl solution ad | 2mg |

We claim:

1. A process for treating painful muscular cramp conditions in an abdominal cavity comprising administering a therapeutic amount of α, α-diphenylacetic acid-4-(N-methyl-piperidyl) ester.

2. A process according to claim 1 for treating painful conditions of a stomach, intestinal spasms or an irritable colon.

3. A process according to claim 1, further comprising administering at least one other therapeutically effective substance together with the therapeutic amount of α,α-diphenylacetic acid-4-(N-methyl-piperidyl) ester.

4. A process according to claim 3, wherein said at least one other therapeutically effective substance comprises an antibiotic or a tranquilizer.

5. A process for using α,α-diphenylacetic acid-4-(N-methyl-piperidyl) ester for production of at least one therapeutically effective drug for treating painful muscular cramp conditions in an abdominal cavity.

6. A process according to claim 5, wherein the painful muscular cramp conditions comprise painful conditions of a stomach, intestinal spasms or an irritable colon.

7. A process according to claim 5, comprising administering said at least one therapeutically effective drug together with at least one other therapeutically effective substance.

8. A process according to claim 7, wherein said at least one other therapeutically effective substance comprises an antibiotic or a tranquilizer.

* * * * *